United States Patent [19]

Smethers et al.

[11] Patent Number: 5,382,512
[45] Date of Patent: Jan. 17, 1995

[54] ASSAY DEVICE WITH CAPTURED PARTICLE REAGENT

[75] Inventors: Rick T. Smethers, Fremont; Brian D. Warner, Martinez, both of Calif.

[73] Assignee: Chiron Corporation, Emeryville, Calif.

[21] Appl. No.: 110,435

[22] Filed: Aug. 23, 1993

[51] Int. Cl.6 .............................................. C12Q 1/68
[52] U.S. Cl. ............................................ 435/6; 422/52; 422/58; 422/102; 422/103; 422/104; 436/805; 436/809; 436/810
[58] Field of Search ............... 422/100, 101, 102, 103, 422/104, 52, 58; 435/6; 436/805, 809, 810

[56] References Cited

U.S. PATENT DOCUMENTS 5,171,537  12/1992  Wainwright .................. 422/100

*Primary Examiner*—Amelia Burgess Yarbrough
*Attorney, Agent, or Firm*—Peter J. Dehlinger; Kenneth M. Goldman; Robert P. Blackburn

[57] ABSTRACT

The invention describes an assay device and assembly for detecting an analyte in a liquid sample. Each assay device in the assembly includes structure defining a well, a ligand-coated particle, and a flexible particle retaining structure for holding the particle in a captured position within the well.

9 Claims, 5 Drawing Sheets

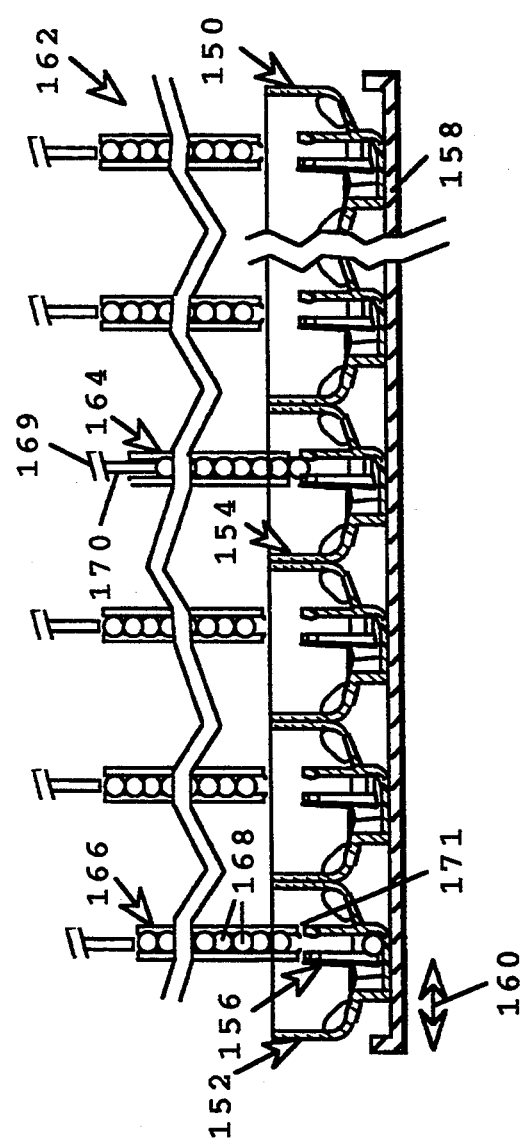

ASSAY DEVICE WITH CAPTURED PARTICLE REAGENT

FIELD OF THE INVENTION

The present invention relates to an assay device for use in detecting an analyte in a liquid sample, and in particular, to a device having a captured particle reagent for use in analyte detection.

BACKGROUND OF THE INVENTION

A variety of solid-phase assay tests for detection or quantitation of solution analytes have been proposed. In a typical test of this type, a test solution is added to a solid-phase reagent which is coated with ligand molecules capable of binding specifically to the analyte, or with molecules effective to compete with the analyte for binding to reporter-labeled anti-ligand molecules. After incubation under binding conditions, the solid-phase reagent is washed to remove unbound sample material, and "developed" to allow detection of analyte or analyte-competing molecules bound to the reagent.

In one general assay format, the solid-phase reagent is a card or multi-well device having a number of surfaces which are coated, e.g., by chemical derivatization, with ligand molecules. In another general format, the solid-phase reagent is a bead or particle coated with ligand molecules. The bead is usually carried in a well, with the various solution addition and removal steps involved in an assay procedure being carried out by careful solution transfer to and from the well.

One advantage of ligand-coated particles, in an solid-phase immunoassay, is that the particles can De prepared more easily in bulk and with greater uniformity, in terms of ligand coating density, than ligand-coated wells or surfaces. Another advantage is that the surface concentration of detectable analyte-related reporter molecules on a particle is effectively higher than on a planar surface, both because of the curvature of the particle and, where the particle is optically transparent, because of the ability to detect reporter molecules on front and back sides of the particle.

It would be desirable to provide an assay device which utilizes ligand-coated particles or beads, to exploit the advantages discussed above, and which also permits easy manufacture, bead capture, and flexibility in designing a system for determination of a selected group of analytes.

SUMMARY OF THE INVENTION

The invention includes, in one aspect, an assay device for use in detecting an analyte in a liquid sample. The device includes wall structure defining a well having a bottom wall and an upper opening, and a particle having surface-bound ligand molecules for use in analyte detection. The device further includes flexible retaining structure attached to said wall structure for retaining the particle in a captured position within the well, when the retaining means is in an undeformed condition, and which can be deformed to admit the particle into the well.

In one general embodiment, the flexible retaining structure includes at least one, and preferably three, flexible finger-like projections disposed between the bottom wall and the opening of the well, where at least one of the projections has an inwardly facing detent dimensioned to hold the particle in a captured position, with the fingers in an undeformed condition. In a related embodiment, at least one of the flexible finger-like projections further includes a second detent positioned and dimensioned to coact with the first-mentioned detent to hold the particle in a raised position above the bottom wall in the well.

In another general embodiment, the particle is a torus with a central opening, and the flexible retaining structure is a stem projecting from said bottom wall, and having a flared distal portion which is deformable to allow receipt of the particle opening onto the stem.

Also in one preferred embodiment, the bottom wall includes a drainage portion from which liquid can be drawn from the well, with the particle captured in the well.

In another aspect, the invention includes a multi-well assembly for detecting one or more analytes in a liquid sample. The assembly includes a plurality of wall structures, each defining a well having a bottom wall, an upper opening, and one or more baffles which separate the well from one or more adjacent wells, respectively. Each baffle is formed of overlapping wall portions which block light transmission, but allow fluid flow, between such adjacent wells.

Each well in the assembly may be designed to hold a particle having surface-bound ligand molecules for use in analyte detection. In a preferred embodiment, each well includes flexible particle-retaining structure, such as described above, for retaining the particle in a captured condition.

In one configuration, the wells in the assembly are arranged in a row, with each pair of adjacent wells being separated by one of the baffles. In another configuration, the wells in the assembly are arranged about a central port region, with each well being separated from this port region by one of the baffles.

In still another aspect, the invention includes a multi-well assay assembly designed for analyte detection, based on chemiluminescence reactions occurring in adjacent wells of the device. The walls of the device separating adjacent wells are formed of polymeric material containing 0.05-0.5 weight percent carbon black.

In still another aspect, the invention includes, a method of carrying out a plurality of solid-phase diagnostic assays for selected analytes. The method includes placing in a predetermined particle-dispensing relationship (i) an assay assembly of the type described above having multiple wells with particle-capture structure, and (ii) a particle dispensing device having a plurality of cartridges, each containing particles coated with a selected ligand. A particle from one or more of the cartridges is dispensed into one or more selected wells in assembly, and each dispensed particle is forced into a captured position in the associated well.

These steps are repeated until particles have been dispensed and captured in a plurality of the wells. The assembly and captured particles are now used for diagnostic assays in each of the particle-containing wells.

These and other objects and features of the present invention will become more fully apparent when the following detailed description of the invention is read in conjunction with the accompanying drawings.

BRIEF DESCRIPTION OF THE FIGURES

FIG. 10 is a schematic view of illustrating a method for distributing selected-analyte beads to selected wells in an assay assembly of the type described above.

DETAILED DESCRIPTION OF THE INVENTION

A. Captured-Bead Assay Device

Figure 1:
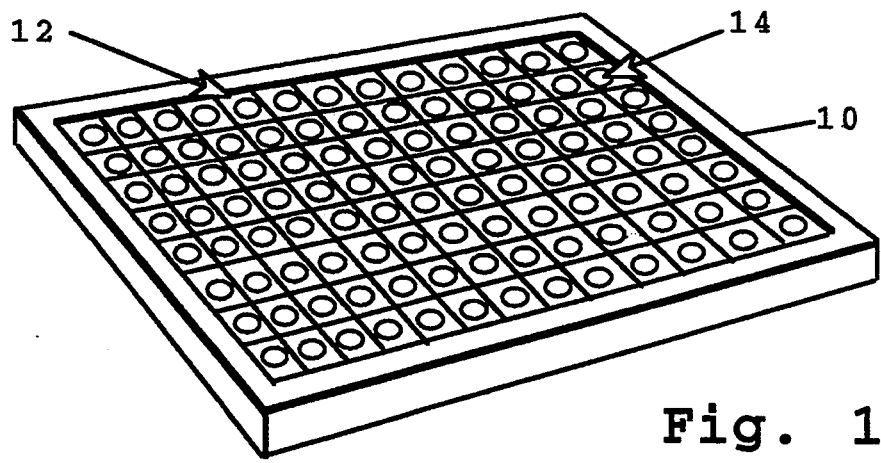
FIG. 1 illustrates a perspective view of a tray containing multi-well assay assemblies constructed in accordance with the invention.

FIG. 1 shows, in perspective view, a tray 10 designed for holding a plurality of multi-well assemblies, such as assemblies 12, 14, constructed in accordance with the invention. In the embodiment shown, the tray is designed to hold eight such assemblies. The tray and loaded assemblies are designed to be used in a multi-well assay reader such as a multi-well luminometer which functions to move the tray in a manner that allows automated, sequential luminescence readings from each well.

Figure 2:
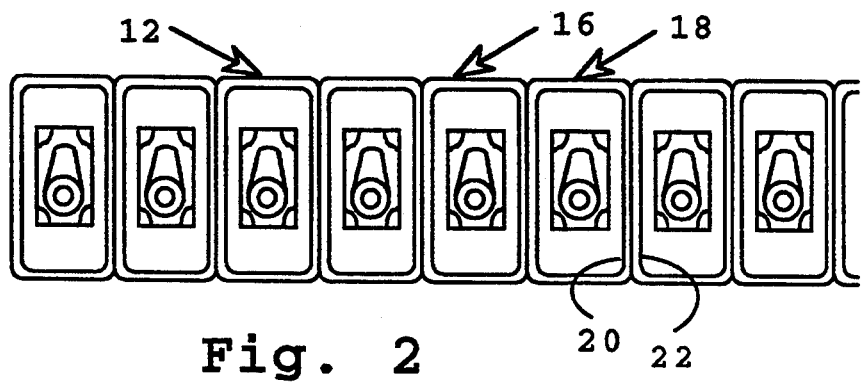
FIG. 2 shows a portion of one of the FIG. 1 assemblies, seen from the top in FIG. 1.
Figure 3:
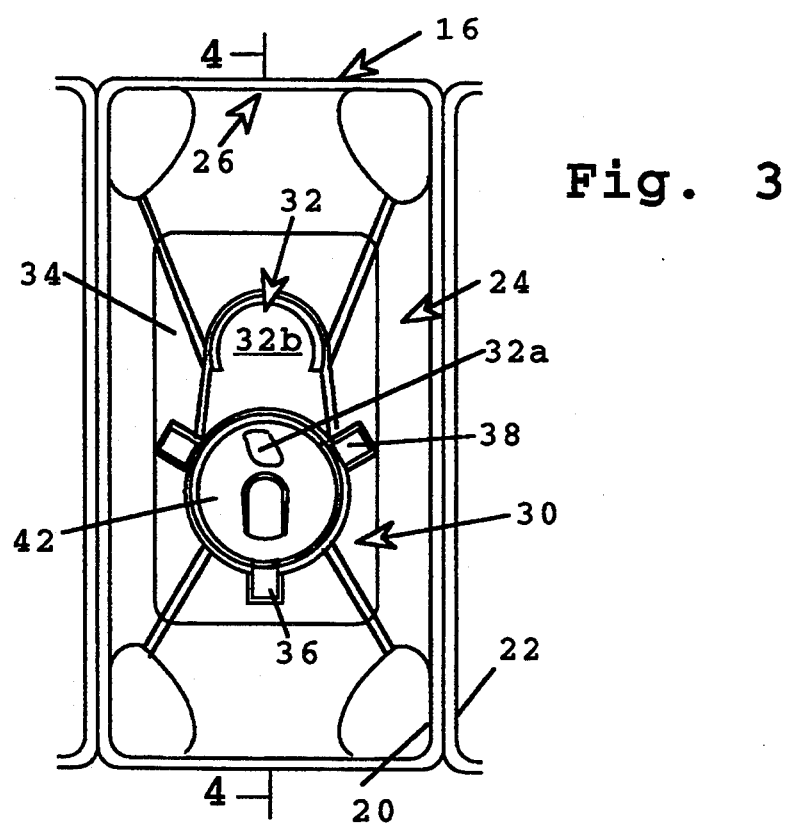
FIG. 3 is an enlarged view of a single-well device in the FIG. 2 assembly.

FIG. 2 shows a plan view of a portion of assembly 12 seen in FIG. 1. The assembly, which is representative, includes a linear array of assay devices, such as devices 16, 18, constructed according to the present invention. The assembly is preferably formed as a single molded plastic article, with the individual devices in the assembly being connected at their upper adjacent edges, such as adjacent edges 20, 22 in devices 16, 18, respectively (FIGS. 2 and 3). In the embodiment shown, the assembly includes 12 assay devices, giving a total of 96 such devices in the fully loaded tray in FIG. 1.

FIG. 3 shows an enlarged plan view of device 16 in assembly 12. The same device is seen cross-sectionally in FIG. 4. The construction of device 16, which is representative, will be illustrated with particular reference to these two figures. As seen, the device includes an elongate well 24 formed by a rectangular wall structure or means 26. The upper edge of the wall structure defines an upper well opening 28. The lower portion of the wall structure, has a reduced width and length which defines a lower well region 30 having a bottom wall 32. The side walls forming the lower region are indicated at 34. The lower well region includes a particle-receiving section 32a, and a liquid-removal section 32b. The bottom wall is sloped to allow fluid in the well region to flow from section 32a toward section 32b, for a purpose to be described.

Figure 4:
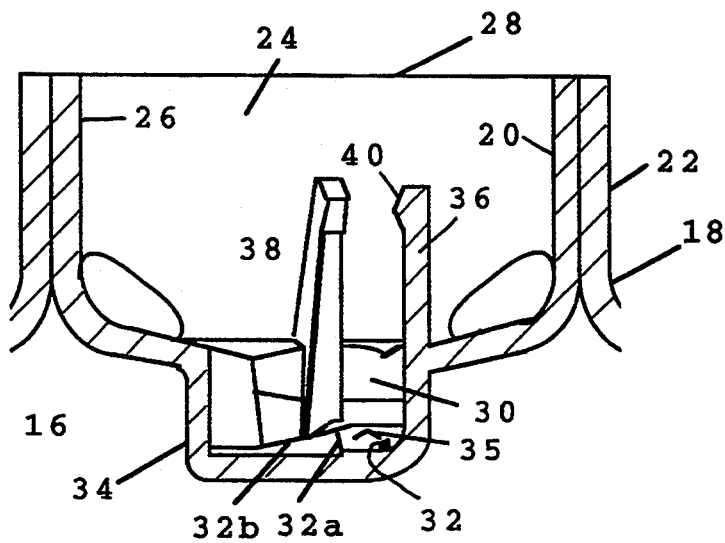
FIG. 4 is an enlarged sectional view of a single-well device, taken along line 4—4 in FIG. 3.

With continued reference to FIGS. 3 and 4, device 16 includes three flexible, finger-like projections, such as projections 36, 38 which project upwardly from the bottom wall of the well toward the well's upper opening. Each projection has an inwardly facing detent, such as detent 40 in projection 36, formed at its free, i.e., upper end. The projections are also referred to herein, collectively, as flexible retaining means. As shown, the three projections are formed integrally with the side walls forming the lower well region, and encompass the particle-receiving section of the well region.

According to an important feature of the invention, an assay particle or bead 42 in the device is received in a captured position in the lower well region by the flexible retaining means which comprise, in the present embodiment, the three flexible finger projections. The bead is supported in the well in a slightly elevated position on a protuberance 35 formed on the bottom of the well, to increase liquid circulation about the particle surface, and enhance analyte capture at surface-bound ligand molecules on the bead in an analyte assay.

The bead is preferably a conventional glass or polymeric bead to which biological assay materials, specifically, surface-bound ligand molecules, can be attached. Typically, the beads have a diameter of between about 1-7 mm. Details of the preparation of the beads, and their role in a particle assay, are given below.

Figure 5A:
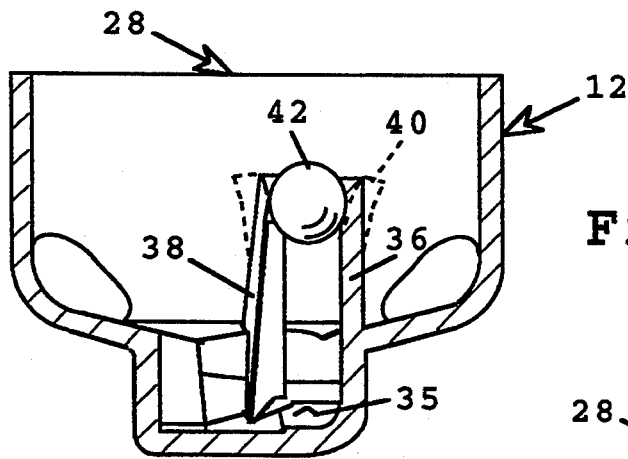
FIGS. 5A and 5B illustrate entry (5A) and capture (5B) of a particle in the device illustrated cross-sectionally in FIG. 4.
Figure 5B:
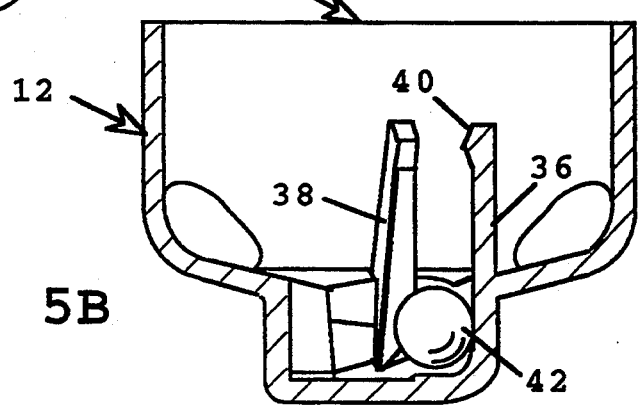

FIGS. 5A and 5B illustrate insertion and capture of bead 42 in device 12. As seen, the bead dimension is such as to force the three finger projections outwardly, to accommodate entry of the bead past the finger-projection detents (FIG. 5A), but allow seating of the bead at the bottom of the well (FIG. 5B). In its captured position, shown in FIG. 5B, the bead is free to rotate and to move vertically between its at rest position on the bottom of the well (in contact with protuberance 35) and a raised position in contact with the lower surfaces of the finger-projection detents.

The construction and scale of the device is preferably such as to allow assays to be performed with small liquid sample volumes, such as 50 to 1000 microliter volumes, sufficient to fill the lower well portion of the device, at least to a level covering bead 42.

As indicated above, the device is preferably formed as a molded polymer article, and also preferably part of a multi-device assembly, such as assembly 12. Where the assembly is employed for chemiluminescent assays, the material forming the assembly is preferably an opaque polymer, such as polyethylene or polyacrylate, containing 4-15 weight percent titanium dioxide. In accordance with one aspect of the invention, it has been discovered that the wells in an assembly can be made completely refractory to chemiluminescent light transmission between wells by addition of between 0.0005 and 0.5 weight percent carbon black to the polymer material used in forming an assembly. The invention includes, in one aspect, a chemiluminescent assay device constructed of an opaque polymer containing titanium dioxide and also containing between 0.0005 to 0.5 weight percent carbon black.

Figure 6:
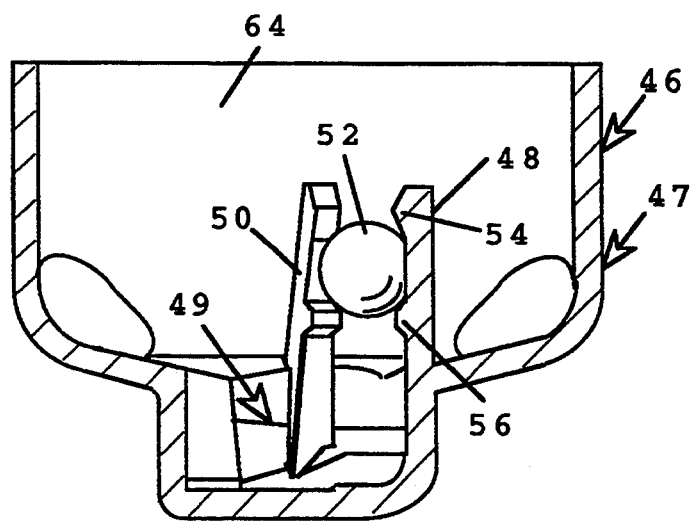
FIG. 6 is a cross-sectional view of a single-well device, like that shown in FIG. 4, but designed for supporting a particle in a raised position in the well.

FIG. 6 shows, in a cross-sectional view similar to that in FIG. 4, a second embodiment of a captured-bead device 46 formed in accordance with the invention. The device has the same general construction as device 12 above, including an identical wall structure 47 defining a well 49. The device differs from device 12 only in the construction of the three flexible, finger-like projections, such as projections 48, 50, used for capturing a particle or bead 52 in the device.

Projection 48, which is representative, has an upper detent 54, similar to detent 40 in projection 36, and a lower detent 56 which is dimensioned, in combination with the lower detents of the other two projections in the device, to capture the bead between the two sets of detents, as shown. The bead can be moved to a second "reaction" position below the lower detents by forcing the bead over the lower detents. The purpose of the two-position feature in an assay will be described below.

Figure 7A:
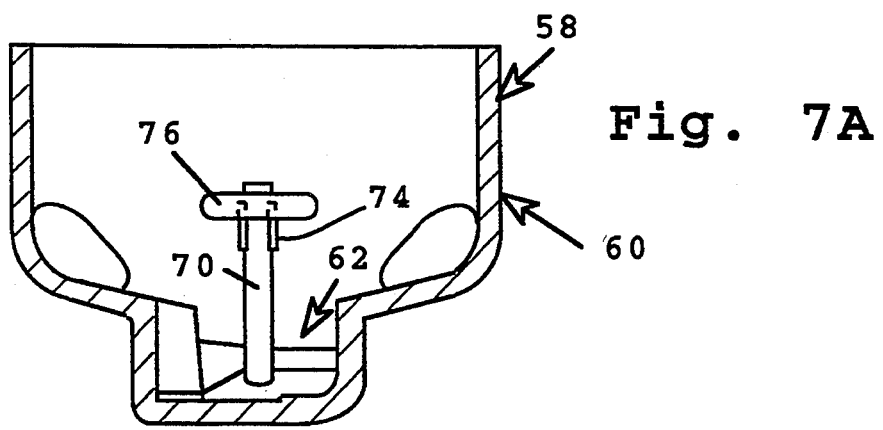
FIGS. 7A and 7B illustrate entry (7A) and capture (7B) of a toroidal particle in a single-well assay device constructed according to a second general embodiment of the invention.
Figure 7B:
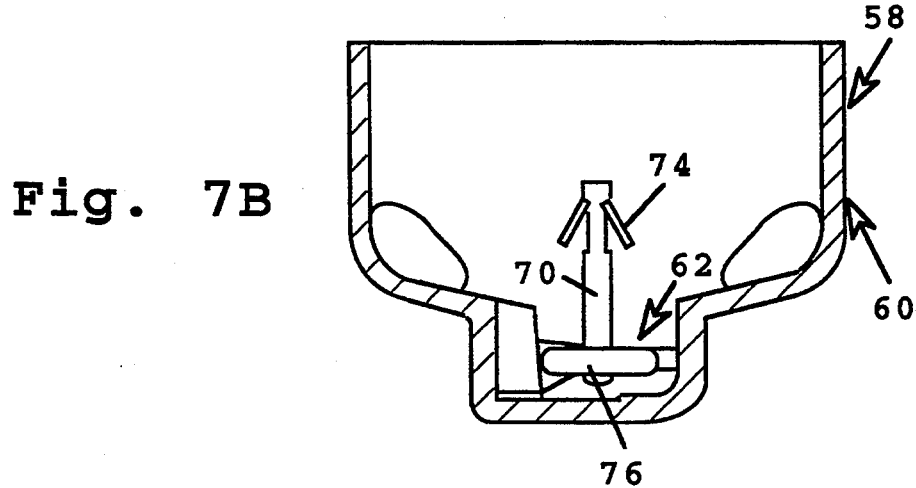

A third embodiment of a bead-capture device constructed according to the invention, and indicated generally at 58, is illustrated in FIGS. 7A and 7B. The device includes wall structure 60 defining a well 62, substantially identical to the wall structure in device 12. The device differs from device 12 in the construction of the assay particle and means for retaining or capturing the particle in the device.

Specifically, the retaining means includes a single vertically extending stem or post 70 which has flexibly movable flared portions 74 cut from and extending away the upper end of the post, in a relaxed condition, as seen in FIG. 7B.

The ligand-coated particle in the device is a toroidal-shaped particle 76 whose interior hole is dimensioned to slide freely over post 70. To place the particle in a captured condition in the device, the particle is placed on the post, as shown in FIG. 7A, with downward movement serving to press portions 74 against the side of the post, in effect deforming the relaxed condition of the portions 74. Once the particle is received on a lower region of the post, the flared portions return to their relaxed conditions, shown in FIG. 7B, acting to prevent the particle from sliding off the post.

In operation of the devices described above, a coated particle, such as particle 42 in FIG. 2, coated with a selected analyte-related ligand, is placed in the well of the device, where the particle becomes captured in the well. The series of sample and test solutions are then added to and removed from the well, employing selected incubation times and reaction temperatures suitable for the particular assay. One exemplary test for detection of a selected-sequence DNA analyte is described in the example below.

As noted above, the particle in the well is exposed fully to each sample or test solution added to the well, by virtue of the slight elevation of the particle in the well, and the ability of the particle to rotate freely in its captured condition. After a selected incubation time, fluid in the well is removed by aspirating from the liquid-removal section 32b of the well, this section acting to drain liquid from the particle-receiving section of the well, to promote substantially complete liquid removal.

The retaining means in the device also acts to restrain the particle in a desired reaction position when sample or test solution is added to the well. In the embodiment illustrated in FIG. 6, the particle may be additional placed at a captured position in the upper portion of the well, to allow chemical-solution mixing and reaction in the well without exposure to the particle.

After the cycle of assay solutions and reactions are completed, the particle is assayed for analyte-related surface reporter groups, typically with the particle submerged in a suitable detection solution, e.g., an enzyme substrate where the captured reporter is an enzyme, as illustrated for the chemiluminescent assay described in the example.

After the assay procedure, the particle may be removed from the well, allowing the device to be reused when washed and loaded with a fresh particle.

B. Connected Well Assembly

In another aspect, the invention includes a multi-well assay assembly having fluid-connected, but light-isolated wells.

Figure 8:
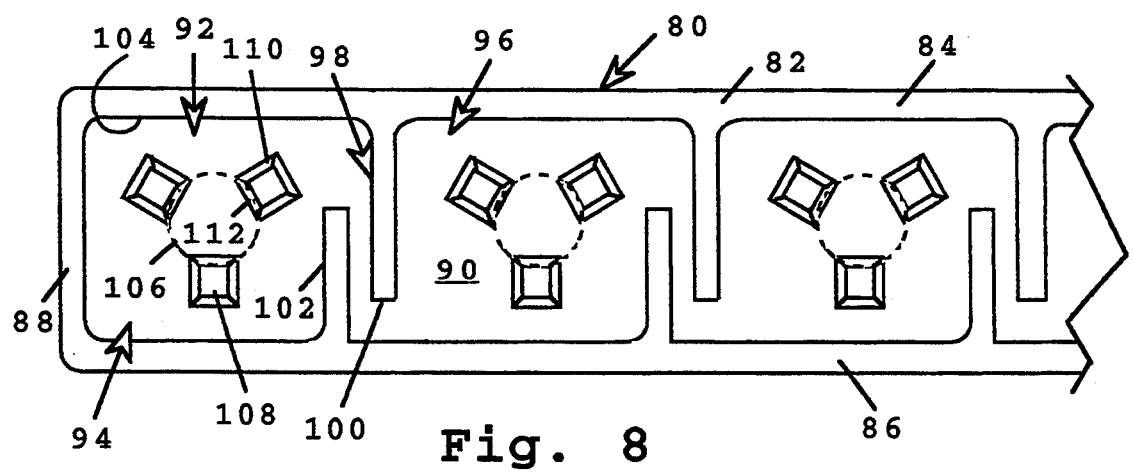
FIG. 8 shows a plan view of a portion of a connected-well assembly having a linear configuration of wells.

FIG. 8 illustrates an assembly 80 formed according to one embodiment of the invention. The assembly includes a multi-well housing 82 having integrally formed side walls, such as walls 84, 86, end walls, such as end wall 88, and a bottom wall 90, collectively forming an elongate channel 92. The channel is divided into a plurality, typically 4–8, wells, such as wells 94, 96 by baffles, such as baffle 98.

As shown, each baffle is formed of a pair of overlapping wall extensions, such as extensions 100, 102 forming baffle 98 and extending from side walls 84, 86, respectively. As can be appreciated from the figure, the baffles allow flow of liquid between adjacent wells, but block direct light transmission from center regions of adjacent wells. The upper edges (those seen in FIG. 8) of the wall portions and baffles defining each well form an upper opening in each well, such as opening 104 in well 94.

In each well, such as well 92, there is provided flexible retaining means for retaining a ligand-coated particle, such as particle 106 shown in dotted lines in the figure. In the embodiment shown, the retaining means includes three finger-like projections, such as projections 108, 110, which are formed integrally with and project upwardly from the bottom wall of the assembly. Each projection has an inwardly facing detent, such as detent 112 on projection 110, dimensioned to hold the particle in a captured position within the well, when the projections are in a relaxed, i.e., undeformed conditions. The fingers can be deformed outwardly, as described above with respect to device 16, to accommodate entry of a particle into the well.

The assembly, including the wall structures, baffles, and retaining means, are preferably formed as a integrally as a molded or injected opaque polymer article. In an assembly employed for chemiluminescent assays, the material forming the assembly preferably contains 0.05 to 0.5 weight percent carbon black, as above, to prevent light contamination through the walls or baffles.

The wall structure defining each well, the retaining means in that well, and the particle captured within the well by the retaining means are also referred to herein as an assay device, such as device 114. Such device differs from device 16 described above in that (a) the bottom walls of each well are flat, rather than sloped, and (b) at least one defining side wall in the device is a baffle, such as baffle 98.

In operation, a coated particle, such as particle 106 is placed in each well of the assembly, where the particle becomes captured in the well. According to an important feature of the invention, the sample and test solutions can be added to and removed from the wells in the assembly from a single well, e.g., well 94, with fluid freely circulating to all of the wells during liquid addition, and being drawn from all of the cells during liquid removal. The advantage of this approach is that all of the wells receive the same solution with each fluid change, improving the uniformity of assay conditions among the several wells.

After the cycle of assay solutions and reactions are completed, the particle is assayed for analyte-related surface reporter groups, as above. Following an assay procedure, the particle may be removed from the well, allowing the device to be reused when loaded with a fresh particle.

Figure 9:
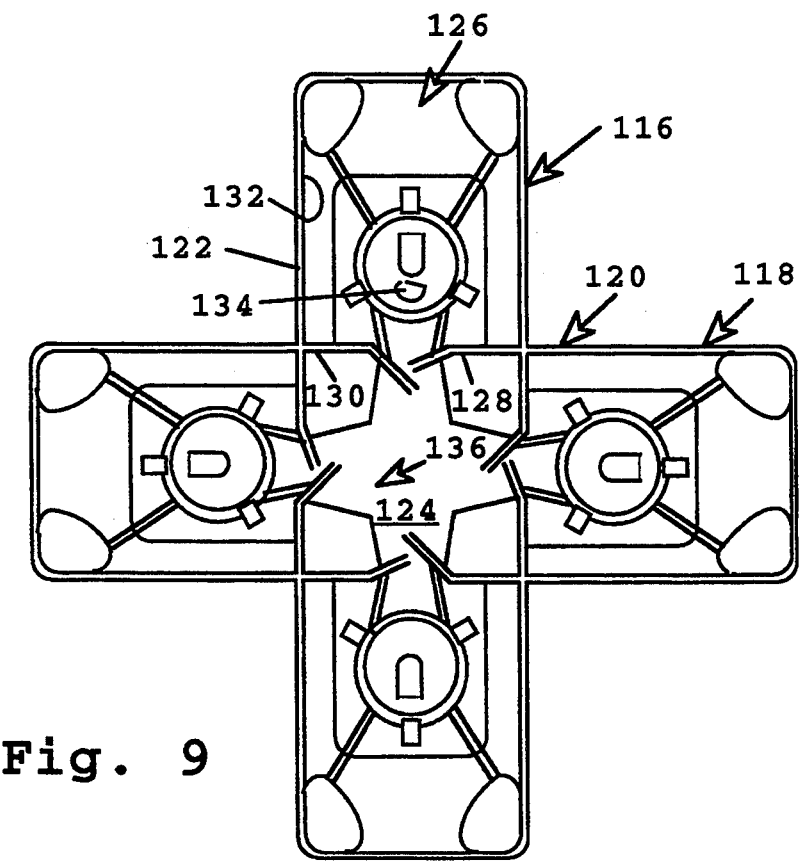
FIG. 9 shows a plan view of a portion of a connected-well assembly having a central-port configuration.
Figure 9:
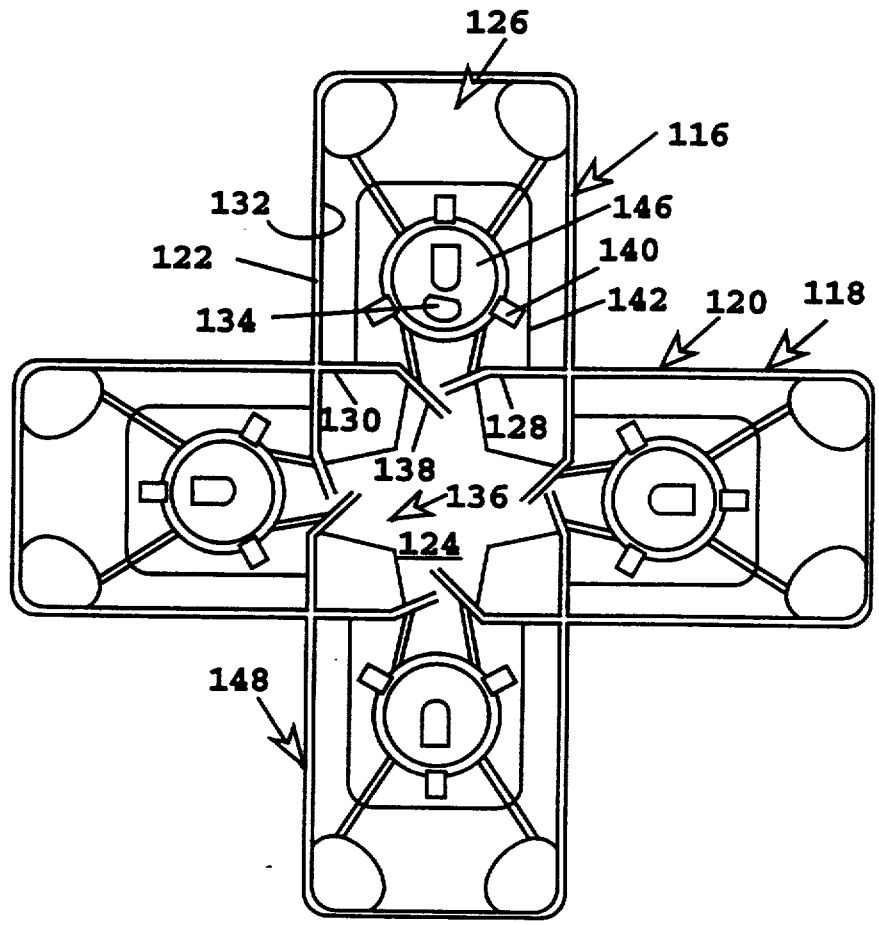

FIG. 9 illustrates another embodiment of a connected-well assembly, here indicated at 116. The assembly includes a multi-well housing 118 having an outer wall 120 formed by four intersecting U-shaped wall portions, such as wall portion 122, and a bottom wall 124. Each wall portion, such as wall portion 122, the underlying bottom wall, and the inwardly projecting end regions of adjacent wall portions, such as end regions 128, 130, form a well, such as well 126, having an upper well opening, such as opening 132. The two end regions defining the inner wall of each well are angled, as shown, to form a baffle, such as baffle 138 in well 126, which allows fluid flow, but blocks light transmission between the well and a central region 136 of the assembly.

The shape of the well is substantially like that of above-described well 24 in device 16, in that the well has a lower, reduced cross-section region, and a bottom wall which slopes downwardly from a particle-receiving region, such as region 134 in well 126, toward the center region of the assembly.

In each well in the assembly, such as well 126, there is provided flexible retaining means for retaining a ligand-coated particle, such as particle 146 shown in the figure. In the embodiment shown, the retaining means includes three finger-like projections, such as projection 140, which are formed integrally with and project upwardly from the bottom wall of the assembly. Each projection has an inwardly facing detent, such as detent 142 on projection 140, dimensioned to hold the particle in a captured position within the well, when the projections are in a relaxed, i.e., undeformed conditions. The fingers can be deformed outwardly, as described about with respect to device 16, to accommodate entry of a particle into the well.

The wall structure defining each well, the retaining means in that well, and the particle captured within the well by the retaining means are also referred to herein as an assay device, such as device 148. Each device is substantially as above described device 16, except for the provision of an inner wall separated from a central area by a light-tight baffle. The assembly is preferably formed as a single molded article, as above.

Operation of the assembly in a multi-sample assay procedure is as described for assembly 80 above, with sample and test liquid being added to and removed from the assembly from central region 136.

C. Coated Particles

Particles employed in the assay devices described above are preferably spherical-bead or toroidal particles. The particles are prepared using known, defined size glass or polymer beads, such as polystyrene, polyacrylamide, polymethyl acrylate, derivatized cellulose fibers, carboxylated polystyrene, polyvinylchloride, polymethylacrylate, polypropylene, latex, polytetrafluorethylene, or polyacrylonitrile beads. In a preferred embodiment, particles are polystyrene beads having ground surfaces to minimize nonspecific molecule binding to the particle surfaces. The particles have a preferred size between about 1–7 mm, preferably about 2–5 mm.

The analyte-related ligand which is bound to the particle surface is one selected to bind specifically with an analyte or a reagent which is capable of competing with the analyte for binding to the particle-bound ligand. The ligand is attached to the particle surface, either covalently or by adsorption, using conventional chemical coupling or surface adsorption methods. One exemplary method for use in attaching DNA ligand molecules to polystyrene beads is given in the example below.

Analyte molecules to be detected typically are nucleic acids, either DNA or RNA, or antigen or antibody analytes. The nucleic acid analytes may be derived from RNA or DNA viruses, bacteria, fungi, or the like, which can infect a specific host. Additionally, the analytes may be derived from the genome of a host which is suspected to contain alleles, mutations or lesions which may make the host susceptible to disease.

The nucleic acid usually contains between 20 and 2000 bases, preferably between 30 and 500 bases. In some cases it may be necessary to digest the sample nucleic acid to the appropriate size prior to the hybridization step. If the nucleic acid analyte is present in double-stranded form the nucleic acid molecule is converted to its single-stranded form by treatment with heat and sodium hydroxide prior to hybridization.

The nucleic acid analytes will typically contain at least one region of sequence complementarity with the nucleic acid ligand molecule which are at least 10 nucleotides in length and up to 1000 nucleotides in length, but typically are of lengths between 15 and 200 nucleotides.

Alternatively, the analytes may be antigens, or other molecules that can be detected by use of antibodies reactive with the molecules. To bind these analytes to a particle surface, first antibodies reactive with the analytes are attached to the surface. To detect surface-bound analytes the particles are incubated with a second a antibody that incorporates a signal-generating label.

In one embodiment of the invention, the particle has a selected specific gravity, e.g., 1 to 1.05, which allows the particle to be floated between raised and lowered captured position, according to the density of assay liquid reagents which are added to wells. For example, it may be desirable to completely submerge the sample during initial phases of an assay, but float the particle to the top of liquid in the well for detecting reporter binding to the particle, at the final step in an assay procedure.

D. Particle-Loading Method

One advantage of the assay assembly described above is the ability to prepare the assembly, on site, for use in a variety of different analyte-assay formats. In one aspect, the invention includes a method for carrying out a plurality of solid-phase diagnostic assays for selected analytes. The method will be described with reference to FIG. 10.

The figure shows a portion of a multi-well assay assembly 150 of the type described, for example, with respect to FIG. 2. Briefly, the assembly includes a plurality of well-defining structures, such as structures 152, 154, which define assay wells and provide flexible particle-retaining structures, such as structure 156. The assembly is carried on a movable platform 158 which can be shifted in the direction of arrow 160 to place the wells in the assembly at selected particle-receiving positions.

Particles are dispensed into the wells by a particle dispensing device 162 having a plurality of cartridges, such as cartridges 164, 166. Each cartridge can be loaded with particles, such as particles 168 in cartridge 166, that are coated with a selected ligand useful for assaying a particular selected analyte. For example, if the analyte to be assayed is a selected antigen, the ligand may be an antibody specific against the analyte antigen. Preferably each cartridge supplies particles having a distinctive surface-bound ligand. The particles are retained in each cartridge by a flexible lip, such as lip 171, at the bottom of cartridge 116.

Each cartridge is shiftable, e.g., under solenoid or pneumatic control, between a raised position, shown for four of the plungers, and a lowered, dispensing position, as shown for plungers 164, 166.

Associated with each cartridge, and shiftable therewith, is a plunger, such as plunger 168 associated with cartridge 164. Each plunger includes a piston, such as piston 170 in plunger 168, which is shiftable, e.g., under solenoid or pneumatic control, from a raised position to a plurality of lowered positions, for dispensing particles from the cartridge, as will be described below.

In operation the assay assembly is shifted to a selected position at which one or more wells in the assembly is positioned to receive a selected-ligand particle from one or more cartridges. Once positioned, the selected cartridge(s) are lowered to a position shown for cartridges 164, 166 in the FIG. 10. For each selected cartridge, the associated piston is shifted to dislodge the lowermost particle from the cartridge, thus dispensing the particle into the well (as shown for cartridge 164 in FIG. 10), with continued piston movement acting to force the dispensed particle into a captured position in the well (as shown for cartridge 166 in FIG. 10).

After this particle dispensing operation, each cartridge is moved to its raised position, and the assembly is moved, by shifting platform 158, to a new position at which one or more unfilled wells are positioned to receive a selected ligand-coated particle from one or more of the cartridges. This process is repeated until a desired number of wells has been filled with selected particles. The assembly is then used in conducting multi-analyte assays, as described above.

The following example illustrates a nucleic acid analyte assay carried out using coated beads of the type suitable for use in the present invention. The example is intended to illustrate, but in no way limit, the scope of the invention.

Example

Bead Assay for HIV Transcript

A. Preparation of Coated Beads

A batch of 1000 3.12 mm polystyrene beads obtained from Hoover Precision Plastics (Sault Ste. Marie, Me.) were soaked in 200 ml of 1 N HCl for one hour at room temperature with agitation at 100 RPM. After washing one time with 1X phosphate buffered saline, the beads were soaked in 200 ml of 1 N NaOH for one hour at room temperature with agitation at 100 RPM. The beads were then washed four times with 1X phosphate buffered saline.

Poly(phe-lys) was purchased from Sigma Chemicals, Inc. (St. Louis, Mo.). This polypeptide has a 1:1 molar ratio of phe:lys and an average m.w. of 47,900 gm/mole. It has an average length of 309 amino acids and contains 155 amines/mole. To 1000 beads was added 10 mg of poly(phe-lys) in 50 mM sodium phosphate buffer pH 7.8 and the mixture was rocked overnight at 4° C.

To 10,000 picomoles of the following oligonucleotide: (SEQ ID NO:1) 3'-CACTTCACTTTCTTT- CCAAGAGX-5, (X is the long chain amine modified nucleotide ($N^4$-(6-aminocaproyl-2-aminoethyl) derivative of 5-methylcytidine)) in 50 mM sodium phosphate pH 7.8 was added 15 mg bis(sulfosuccinimidyl) suberate ($BS^3$). The mixture was vortexed and incubated at room temperature for 30 min. A gel filtration column (NAP-25; Pharmacia) equilibrated with 10 mM sodium phosphate pH 6.5 was used to purify the activated oligonucleotide. The activated oligonucleotide reaction mixture was applied to the column and allowed to filter. The eluate was collected and diluted to 100 ml with 50 ml sodium phosphate, pH 7.8 and added to the beads. The mixture was incubated at 4° C. overnight with agitation. The beads were then washed four times with 1X phosphate buffered saline.

In order to strip the derivatized bead of loosely bound DNA, the following wash steps were employed. 1000 beads were processed in a 300 ml final volume of 0.2N NaOH, 0.5% SDS for 1.5 hours at 63° C. with agitation. After cooling at room temperature for 10 min the beads were washed four times with 1X phosphate buffered saline. The beads were then overcoupled using 50 mg/100 ml of $BS^3$ in 50 mM sodium phosphate buffer, pH 7.8, at 4° C. overnight with agitation. The beads were washed four times with 1X phosphate buffered saline, then dried at 37° C. and stored at 4° C.

B. Hybridization Assay

As a target, a synthetic RNA transcript (containing the pol region of HIV-1 sequence) was prepared and used at $1.2 \times 10^6$, $6.0 \times 10^5$ and $3 \times 10^5$ copies/ml. The negative control contained no target RNA.

Sample preparation consisted of delivering 300 µl of 60 units/ml proteinase K in 175 mM HEPES, pH 7.5, 14 mM EDTA, 1.75% lithium lauryl sulfate, 1.025M lithium chloride, and 33 fmoles capture extender probes specific for HIV pol region (each), 555 fmole label extender probes specific for HIV pol region (each) to each well containing a DNA coated bead. 100 µl of RNA in the amounts listed above, diluted in negative human plasma, was then added to the wells. Wells were agitated to mix the contents, covered and incubated for 16 hr at 63° C.

After a further 10 minute period at room temperature, the contents of each well were aspirated to remove all fluid, and the wells washed 2X with washing buffer (0.1% SDS, 0.015M NaCl, 0.0015M sodium citrate). A branched DNA signal amplification multimer was then added to each well (50 µl of 600 fmol/ml solution in 0.6M NaCl, 0.06M sodium citrate, 1.3% SDS, 50% horse serum). After covering the plates and agitating to mix the contents in the wells, the plates were incubated for 30 min at 53° C.

After a further one minute period at room temperature, the wells were washed as described above.

Alkaline phosphatase label probe, disclosed in EP 883096976, was then added to each well (50 µl of 500 fmol/ml solution in 0.6M NaCl, 0.06M sodium citrate, 1.3% SDS, 50% horse serum). After incubation at 53° C. for 15 min, and 10 min at room temperature, the wells were washed three times as above and then three times with 0.015M NaCl/0.0015M sodium citrate.

An enzyme-triggered dioxetane (Schaap et al., Tet. Lett. (1987) 28:1159–1162 and EPA Pub. No. 0254051), obtained from Lumigen, Inc., was employed. 50 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 20-40 min.

The light output from the dioxetane reagent was then read on a luminometer. Output was given as the full integral of the light produced during the reaction, with the results given in the table below,.

| HIV RNA Copies/ml | Luminescence Units |
|---|---|
| $1.2 \times 10^6$ | 1.6 |
| $6.0 \times 10^5$ | 0.92 |
| $3.0 \times 10^5$ | 0.53 |
| 0 | 0.11 |

While the invention has been described with reference to specific methods and embodiments, it will be appreciated that various modifications and changes may be made without departing from the invention.

It is claimed:

1. An assay device for use in detecting an analyte in a liquid sample by means of a detectable reaction that is related to the amount of analyte present in the sample, comprising wall means defining a well having a bottom wall and an upper opening through which such a reaction can be detected, a particle having surface-bound ligand molecules for use in analyte detection, said particle being supported on said bottom wall, and flexible retaining means attached to said wall means, for retaining said particle in a captured position within said well, when the retaining means is in an undeformed condition, and which can be deformed to admit said particle into the well.

2. The device of claim 1, wherein said flexible retaining means includes finger-like projection means extending from said bottom wall in the direction of said upper opening.

3. The device of claim 2, wherein said finger-like projection means includes three flexible projections extending from said bottom wall in the direction of said upper opening and terminating at free ends, where at least one of said projections has an inwardly facing detente dimensioned to hold the particle in a captured position, with said projections in an undeformed condition.

4. The device of claim 3, wherein at least one of the three flexible finger-like projections further includes a second detent positioned and dimensioned to coact with the first-mentioned detent to hold said particle in a raised position above said bottom wall in said well.

5. The device of claim 1, wherein said particle is a torus with a central opening, and said flexible retaining means is a stem projecting from said bottom wall, and having a flared distal portion which is compressible to allow receipt of the particle opening onto said stem.

6. The device of claim 1, wherein said bottom wall includes a drainage portion from which liquid can be drawn from the well, with the particle captured in the well.

7. The device of claim 1, which further includes a means formed on said bottom wall, effective to support said particle in an elevated position in the well.

8. The device of claim 1, for use in detecting a nucleic acid analyte, wherein the ligand molecules are single-stranded nucleic acid molecules including sequence complementarity to said nucleic acid analyte.

9. The device of claim 1, wherein said analyte is detected by a chemiluminescence detector, and said wall means are constructed of an opaque polymer.

* * * * *

UNITED STATES PATENT AND TRADEMARK OFFICE
CERTIFICATE OF CORRECTION

PATENT NO. : 5,382,512

DATED : Jan. 17, 1995

INVENTOR(S) : Rick T. Smethers and Brian D. Warner

It is certified that error appears in the above-identified patent and that said Letters Patent is hereby corrected as shown below:

Fig. 9 should appear as per attached:
insertion of numerical indications for elements
138, 140, 142, 146 and 148.

Signed and Sealed this

Twelfth Day of November, 1996

Attest:

BRUCE LEHMAN

Attesting Officer

Commissioner of Patents and Trademarks